United States Patent [19]

Hochlowski et al.

[11] Patent Number: 5,484,799
[45] Date of Patent: Jan. 16, 1996

[54] ANTIFUNGAL DORRIGOCIN DERIVATIVES

[75] Inventors: Jill E. Hochlowski, Green Oaks; Marianna Jackson, Waukegan, both of Ill.; Sunil K. Kadam, Kenosha, Wis.; James P. Karwowski, Mundelein; James B. McAlpine, Libertyville, both of Ill.

[73] Assignee: Abbott Laboratories, Abbott Park, Ill.

[21] Appl. No.: 164,234

[22] Filed: Dec. 9, 1993

[51] Int. Cl.⁶ .......................... A61K 31/44; A61K 31/45; C07D 211/40; C07D 211/76
[52] U.S. Cl. .......................... 514/345; 514/335; 546/243; 546/296; 435/117; 435/240.2
[58] Field of Search ..................... 546/243, 296; 514/335, 345

[56] References Cited

U.S. PATENT DOCUMENTS 5,002,959  3/1991  Konishi et al. ..................... 514/326

OTHER PUBLICATIONS

Chemical Abstracts, vol. 81(1) Abst. No. 2395–d Jul. 08, 1974.
Urakawa et al., Journal of Antibiotics, vol. 46, No. 12, pp. 1827–1833 Dec. 1993.

*Primary Examiner*—Alan L. Rotman
*Attorney, Agent, or Firm*—Thomas D. Brainard; Andreas M. Danckers

[57] ABSTRACT

Novel antifungal and antitumor agents having the formula

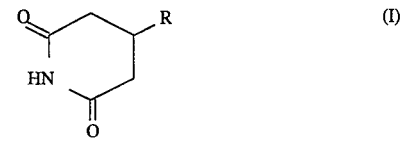

as well as pharmaceutically acceptable salts, esters, amides and pro-drugs thereof, wherein R is selected from the group consisting of

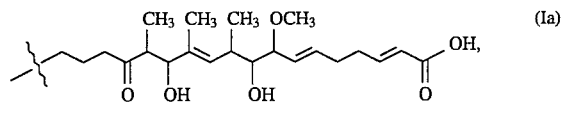

and

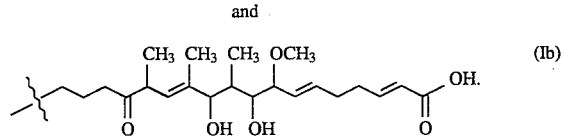

Also disclosed are pharmaceutical compositions comprising such compounds, and methods of treatment and processes of manufacture relating thereto.

5 Claims, No Drawings

ANTIFUNGAL DORRIGOCIN DERIVATIVES

Technical Field

The present invention relates to novel compounds isolated from cultures of the genus Stretomyces, herein designated "dorrigocins", which possess antifungal and antitumor activity. The invention also relates to methods and cultures of microoganisms useful for the preparation of dorrigocins, as well as to pharmaceutical compositions containing such compounds and the use thereof in treating fungal infections and tumors.

BACKGROUND OF THE INVENTION

Certain compounds of the glutarimide class have been demonstrated to have antimicrobial activity. Known glutarimide antibiotics include the following compounds: cycloheximide, disclosed by Leach et al., *J. Amer. Chem. Soc.* 69:474 (1947); streptimidone, disclosed by Frohardt et al., *J. Amer. Chem. Soc.* 81:5500 (1959);9-methylstreptimidone, disclosed by Saito et al., *J. Antibiotics* 27 (3):206 (1974); S-632-$B_1$ and S-632-$B_2$, disclosed by Otani et al., *J. Antibiotics* 43:654 (1989); and BU-4146T, disclosed by Konishi et al., in U.S. Pat. No. 5,002,959, issued Mar. 26, 1991. There remains, however, a continued need for antibiotics having novel spectra of activity and/or different therapeutic applicability.

SUMMARY OF THE INVENTION

It has now been found that novel compounds of the glutarimide class may be obtained by fermentation of certain cultures belonging to the genus Streptomyces. These compounds have been shown to possess antifungal and antitumor activity.

Accordingly, in one aspect of the present invention are disclosed compounds having the formula

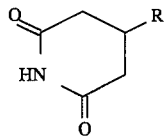

as well as pharmaceutically acceptable salts, esters, amides and pro-drugs thereof, in which the radical R is selected from the group consisting of

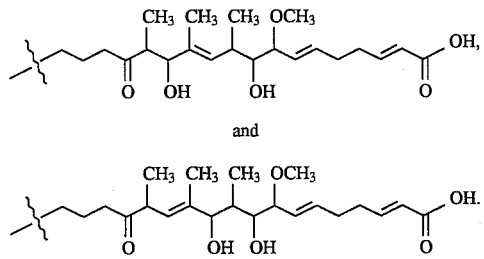

In another aspect of the present invention are disclosed pharmaceutical compositions which comprise a therapeutically effective amount of a compound of the invention in combination with a pharmaceutically acceptable carrier.

In another aspect of the invention is disclosed a method of inhibiting fungal infections in a patient in need of such treatment, comprising administering to the patient a therapeutically effective amount of a compound of the invention.

In a further aspect of the invention is disclosed a method of inhibiting tumor development in a patient in need of such treatment, comprising administering to the patient a therapeutically effective amount of a compound of the invention. Alternatively, a method is disclosed for causing reversion of transformed, tumor-type cells to cells having a normal morphology, comprising exposing the tumor-type cells to a compound according to claim 1 in a concentration sufficient to produce the desked reversion.

In yet another aspect of the invention is disclosed a process for the preparation of a compound of the invention which comprises the steps of (a) culturing a microorganism having all the identifying characteristics of Streptomyces species strain NRRL 18993 under suitable conditions in a fermentation medium containing assimilable sources of carbon and nitrogen; (b) allowing the compound to accumulate in the fermentation medium; and (c) isolating the compound from the fermentation medium. Also disclosed is a biologically pure culture of a microorganism capable of producing the compounds of the invention, namely, *Streptomyces* species strain NRRL 18993, free from any biologically active contaminant.

DETAILED DESCRIPTION OF THE INVENTION

The term "pharmaceutically acceptable salts, esters, amides and prodrugs" as used herein refers to those carboxylate salts, amino acid addition salts, esters, amides and prodrags of the compounds of the present invention which are, within the scope of sound medical judgement, suitable for use in contact with with the tissues of humans and lower animals with undue toxicity, irritation, allergic response, and the like, commensurate with a reasonable benefit/risk ratio, and effective for their intended use, as well as the zwitterionic forms, where possible, of the compounds of the invention.

The term "salts" refers to the relatively non-toxic, inorganic and organic acid addition salts of compounds of the present invention. These salts can be prepared in situ during the final isolation and purification of the compounds, or by separately macring the purified compound in its free base form with a suitable organic or inorganic acid and isolating the salt thus formed. Representative salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate and laurylsulphonate salts and the like. These may include cations based on the alkali and alkaline earth metals, such as sodium, lithium, potassium, calcium, magnesium and the like, as well as nontoxic ammonium, quaternary ammonium and amine cations including, but not limited to, ammonium, tetramethylammonium, tetraethylammonium, methylamine, dimethylamine, trimethylamine, triethylamine, ethylamine and the like. (See, for example S. M. Berge et al., "Pharmaceutical Salts," *J. Pharm. Sci.* 66:1–19 (1977), which is incorporated herein by reference.)

Examples of pharmaceutically acceptable, non-toxic esters of the compounds of this invention include $C_1$-to-$C_6$ alkyl esters wherein the alkyl group is a straight or branched chain; $C_1$-to-$C_4$ alkyl esters are preferred. Acceptable esters also include $C_5$-$C_7$ cycloalkyl esters as well as arylalkyl esters including, but not limited to, benzyl. Esters of the compounds of the present invention may be prepared according to conventional methods.

Examples of pharmaceutically acceptable, non-toxic amides of the compounds of this invention include amides derived from ammonia, primary $C_1$-to-$C_6$ alkyl amines and secondary $C_1$-to-$C_6$ dialkyl amines wherein file alkyl groups are straight or branched chain. In the case of secondary amines the amine may also be in the form of a 5- or 6-membered heterocycle containing one nitrogen atom. Amides derived from ammonia, $C_1$-to-$C_3$ alkyl primary amides and $C_1$-to -$C_2$ dialkyl secondary amides are preferred. Amides of the compounds of the invention may be prepared according to conventional methods.

The term "prodrug" refers to compounds that are rapidly transformed in vivo to yield the parent compound of the above formula, for example by hydrolysis in blood. A thorough discussion is provided in T. Higuchi and V. Stella, *Pro-drugs as Novel Delivery Systems*, Vol. 14 of the A.C.S. Symposium Series, and in Edward B. Roche, ed., *Bioreversible Carriers in Drug Design*, American Pharmaceutical Association and Pergamon Press (1987), both of which are incorporated herein by reference.

Where appropriate, prodrugs of derivatives of compounds of the present invention may be prepared by any suitable method. For those compounds in which the prodrug moiety is an amino acid or peptide functionality, the condensation of the amino group with amino acids and peptides may be effected in accordance with conventional condensation methods such as the azide method, the mixed acid anhydride method, the DCC (dicyclohexyl-carbodiimide) method, the active ester method (p-nitrophenyl ester method, N-hydroxy-succinic acid imide ester method, cyanomethyl ester method and the like), the Woodward reagent K method, the DCC-HOBT (1-hydroxy-benzotriazole) method and the like. Classical methods for amino acid condensation reactions are described in M. Bodansky, Y. S. Klausner and M. A. Ondetti, *Peptide Synthesis*, Second Edition. NY (1976).

The compounds of the invention exhibit in vitro activity as antifungal agents against a variety of fingal organisms, and as antitumor agents in an in vitro assay utilizing K-ras-transformed NIH/3T3 mouse fibroblasts. They are therefore expected to be useful in the treatment of fungal infections and tumors in mammals.

When used in the above or other treatments, a therapeutically effective amount of one of the compounds of the present invention may be employed in pure form or, where such forms exist, in pharmaceutically acceptable salt, ester or prodrug form. Alternatively, the compound may be administered as pharmaceutical compositions containing the compound of interest in combination with one or more pharmaceutically acceptable excipients. By a "therapeutically effective amount" of the compound of the invention is meant a sufficient amount of the compound to treat the targeted disorder, at a reasonable benefit/risk ratio applicable to any medical treatment.

In the case of antifungal therapy, it is expected that the compounds of the present invention may be administered to a human patient at a rate of from 1 to 100 mg/kg/day and, more preferably, of from 2 to 10 mg/kg/day. As antitumor agents, the compounds of the invention may be administered to a human patient at a rate of from 2 to 2000 mg/kg/day and, more preferably, of from 20 to 200 mg/kg/day. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

The pharmaceutical compositions of the present invention comprise a compound of the invention in combination with a pharmaceutically acceptable carrier or excipient, which may be administered orally, rectally, parenterally, intracisternally, intravaginally, intraperitoneally, topically (as by powders, ointments, or drops), bucally, or as an oral or nasal spray. By "pharmaceutically acceptable carrier" is meant a non-toxic solid, semi-solid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Pharmaceutical compositions of this invention for parenteral injection include pharmaceutically acceptable sterile nonaqueous solutions or aqueous dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservative, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents which delay absorption such as aluminum monostearate and gelatin.

In some cases, in order to prolong the effect of the drug, it is desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly-(orthoesters) and poly(anhydrides) Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose and acacia, c) humectants such as glycerol, d) disintegrating agents such as agar-agar, calcium carbonate, potato or tapioca starch, alginic acid, certain silicates and sodium carbonate, e)solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols and sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, and sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, may be prepared as a dry powder which may be pressurized or non-pressurized. In non-pressurized powder compositions, the active ingredient in finely divided form may be used in admixture with a larger-sized pharmaceutically acceptable inert carrier comprising particles having a size, for example, of up to 100 micrometers in diameter. Suitable inert carriers include sugars such as lactose. Desirably, at least 95% by weight of the particles of the active ingredient have an effective particle size in the range of 0.01 to 10 micrometers.

Alternatively, the composition may be pressurized and contain a compressed gas, such as nitrogen or a liquified gas propellant. The liquified propellant medium and indeed the total composition is preferably such that the active irradient does not dissolve therein to any substantial extent. The pressurized composition may also contain a surface active agent. The surface active agent may be a liquid or solid non-ionic surface active agent or may be a solid anionic surface active agent. It is preferred to use the solid anionic surface active agent in the form of a sodium salt.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients, and the like. The preferred lipids are the phospholipids and the phosphatidyl cholines (lecithins), both natural and synthetic. Methods to form liposomes are known in the art. See, for example, Prescott, ed., *Methods in Cell Biology*, Volume XIV, p. 33 et seq., Academic Press, N.Y., N.Y. (1976).

The compounds of the present invention, which have been given the name "dorrigocins", are produced by a strain of *Streptomyces platensis* subsp. *rosaceus* subsp. nov., which was isolated from a soil sample collected from the Dorrigo Plateau in New South Wales, Australia. A subculture of this microorganism was deposited on Aug. 31, 1992, in the permanent collection of the National Center for Agricultural Utilization Research, United States Department of Agriculture, 1815 North University Street, Peoria, Ill. 61604, U.S.A., under the terms of the Budapest Treaty. This subculture, which produces dorrigocins A and B, has been given accession number NRRL 18993.

Characterization of the Organism

Cultural and physiological characteristics of strain NRRL 18993 were examined using the methods and media described by Shifting and Gottlieb (*Int. J. Syst. Bacteriol.*, 16:313–340 (1966)), Waksman (*The Actinomycetes*, Vol. 2, pp 328–334, Williams & Wilkins, Baltimore (1961)) and Gordon et al. (*Int. J. Syst. Bacteriol.*, 24:54–63 (1974)). Incubation for cultural characteristics and carbon utilization was at 28° C. for 14 days. Production of $H_2S$ was determined on ISP-6 agar by method 2 of Smibert and Krieg (*Manual of Methods for General Bacteriology*, pp 409–443, American Society for Microbiology, Washington, D.C. (1981)) and Kutzner's technique (*The Prokaryotes*, pp. 2028–2090, Springer Verlag, N.Y. (1981)) was used to observe reduction of nitrate. Analysis of the whole-cell diaminopimelic acid isomer was done by the method of Hasegawa et al. (*J. Gen. Appl. Microbiol.*, 29:319–332 (1983)). The characteristics of strain NRRL 18993 are as follows:

Morphology: The vegetative mycelium of strain NRRL 18993 is well developed and does not fragment. The aerial mycelium is monopodially branched and forms clusters of tightly coiled spore chains. The spore chains usually have 4 to 5 turns and contain more than 10 spores. This morphology is seen on yeast extract-malt extract, oatmeal and inorganic salts/starch agars. No spores were observed on glycerol-asparagine agar. Scanning electron microscopy showed that the spores have a smooth surface, are elliptical to half-moon or crescent-shaped and typically measure 0.7 μm×1.0 μm. The culture forms unusual coalesced masses on some media that appear to be tangles of mycelia. No sporangia or zoospores were observed.

Chemotaxonomy: A whole cell hydrolysate contained major amounts of LL-diaminopimelic acid.

Utilization of carbon sources, cultural and physiological characteristics: The carbon source utilization pattern, cultural characteristics and physiological characteristics of strain NRRL 18993 are given in tables 1, 2 and 3 respectively. A review of the literature indicated that strain NRRL 18993 resembled S. platensis; therefore a comparison was made between our new strain and the type strain S. platensis ATCC 13865, and the data for the two strains are reported in the tables. The aerial roycelia of strain NRRL 18993 was light pink to purplish gray on yeast extract-malt extract md inorganic salts-starch agars. Brown to black hygroscopic patches were formed on oatmeal agar. The reverse was dark brown modified by red on ISP-2 and ISP-4, dark orange yellow on ISP-3 and yellowish white on ISP-5 agar. The reverse mycelial pigments were not pH sensitive. A reddish brown soluble pigment, which was also not pH sensitive, was produced on yeast extract-malt extract agar. Light yellow or brown soluble pigments were formed on several other media. Melanoid pigments were not produced in tryptone-yeast extract broth or peptone-yeast extract iron and tyrosine agars.

Taxonomic position: The morphological and chemical characteristics of strain NRRL 18993 indicated that it belongs to the genus Streptornyces Waksman and Henrici, 1943. Based on several keys used to identify Streptomyces species, it was obvious that strain NRRL 18993 was similar to S. platensis Tresner and Backus (Appl. Microbiol., 4: 243–250, 1956). Tables 1 and 3 show that both cultures have the :same carbon utilization pattern but differ in growth temperature range, milk peptonization and gelatin liquefaction among the physiological characteristics examined. A striking difference between the two strains, however, is the color of the aerial. mycelium on yeast extract-malt extract, inorganic salts-starch and sucrose nitrate agar media. The aerial mycelium of the type strain S. platensis ATCC 13865 is dark brown or gray while strain NRRL 18993 forms much lighter pink and purplish gray pigments on these media. Strain NRRL 18993 has been designated Streptomyces platensis subsp. rosaceussubsp. nov. in recognition of this pink color of its aerial mycelium.

TABLE 1

Utilization of carbon sources by strain NRRL 18993 and Type Strain Streptomyces platensis ATCC 13865

| Carbon Source | NRRL 18993 | ATCC 13865 |
|---|---|---|
| Adonitol | − | − |
| L-Arabinose | + | + |
| Dulcitol | − | − |
| D-Fructose | ++ | ++ |
| D-Galactose | ++ | ++ |
| D-Glucose | ++ | ++ |
| m-Inositol | ++ | ++ |
| D-Mannitol | ++ | ++ |
| D-Melezitose | ++ | ++ |
| D-Melibiose | ++ | ++ |
| D-Raffinose | ++ | ++ |
| L-Rhamnose | − | − |
| Salicin | + | + |
| Sucrose | ++ | ++ |
| Xylitol | ++ | ++ |
| D-Xylose | ++ | + |

"++" = Good utilization;
"+" = poor utilization;
"−" = did not utilize

TABLE 2

Comparative cultural characterisics of strain NRRL 18993 and Type Strain Streptomyces platensis ATCC 13865

| Medium | Abbr | NRRL 18993 | ATYCC 13865 |
|---|---|---|---|
| Yeast extract-malt extract agar (ISP-2) | G* | Abundant | Abundant |
| | AM | Pinkish white (9)** and purplish gray (233); sporulated | Brownish gray (64); sporulated |
| | R | Dark reddish brown (44) | Deep yellowish brown (75) |
| | SP | Light reddish brown (42) | Light reddish brown (42) |
| Oatmeal agar (ISP-3) | G | Moderate | Moderate |
| | AM | Dark yellowish brown (78) and purplish gray (233) with brownish black (65) moist specks; sporulated | Dark yellowish brown (78), moist; sporulated |
| | R | Dark orange yellow (72) | Light grayish reddish brown (45) |
| | SP | Light yellowish brown (76) | Light yellowish brown (76) |
| Inorganic salts-starch agar (ISP-4) | G | Abundant | Abundant |
| | AM | Pinkish white (9) and purplish gray (233); sporulated | Light grayish reddish brown (45) to brownish black (65); sporulated |
| | R | Grayish reddsh brown (46) | Grayish brown (61) |
| | SP | Light yellowish brown (76) | Light yellowish brown (76) |
| Glycerol-asparagine agar (ISP-5) | G | Poor | Poor |
| | AM | Pinkish white (9); not sporulated | Pinkish white (9); not sporulated |
| | R | Yellowish white (92) | Yellowish white (92) |
| | SP | Absent | Absent |
| Peptone-yeast extract iron agar (ISP-6) | G | Moderate | Moderate |
| | AM | Purplish white (231) | Purplish white (231) |
| | R | Light orange yellow (70) | Light orange yellow (70) |
| | SP | Absent | Absent |
| Tyrosine agar (ISP-7) | G | Moderate | Moderate |
| | AM | Purplish white (231) | Purplish white (231) |
| | R | Yellowish white (92) | Yellowish white (92) |
| | SP | Absent | Absent |

TABLE 2-continued

Comparative cultural characterisics of strain NRRL 18993
and Type Strain *Streptomyces platensis* ATCC 13865

| Medium | Abbr | NRRL 18993 | ATYCC 13865 |
|---|---|---|---|
| Bennett's agar | G | Abundant | Abundant |
| | AM | Purplish gray (233) | Light grayish reddish brown (45) |
| | R | Dark reddish brown (44) | Moderate reddish brown (43) |
| | SP | Light yellowish brown (76) | Light yellowish brown (76) |
| Sucrose nitrate agar | G | Moderate | Moderate |
| | AM | Pale pink (7) to grayish red (19) | Dark reddish gray (22) |
| | R | Pale pink (7) and grayish red (19) | Light grayish reddish brown (45 |
| | SP | Pale orange yellow (73) | Absent |
| Glucose-asparagine agar | G | Moderate | Moderate |
| | AM | Grayish pink (8) | Grayish pink (8) |
| | R | Moderate brown (58) | Pale orange yellow to (73) moderate brown (58) |
| | SP | Absent | Absent |
| Nutrient agar | G | Moderate | Moderate |
| | AM | Pale pink (7) | Dark orange yellow (72) |
| | R | Pale yellow (89) | Pale orange yellow (73) |
| | SP | Absent | Absent |

*Abbreviations:
G = growth,
AM = aerial mycelium,
R = reverse,
SP = soluble pigment
**Color and number in parenthesis follow the color standard in Kelly, K. L. & D. B. Judd, ISCC-NBS Color-Name Charts Illustrated with Centroid Colors, U.S. Dept. of Comm. Suppl. to Cir. 553, Washington, D.C., 1976.

TABLE 3

Comparative physiological characteristics of strain NRRL 18993
and Type Strain *Streptomyces platensis* ATCC 13865

| Test | NRRL 18993 | ATCC 13865. |
|---|---|---|
| Decomposition of: | | |
| Casein | + | + |
| Hypoxanthine | + | + |
| L-Tyrosine | + | + |
| Xanthine | + | + |
| Adenine | + | + |
| Starch hydrolysis | + | + |
| Nitrate reduction | + | + |
| Milk peptonization | + | − |
| Milk Coagulation | − | − |
| Gelatin (4%) liquefaction | + | − |
| H$_2$S production | − | − |
| Temperature range for growth (on ISP-2) | 10°–32° C.; no growth at 4° and 37° C. | 15°–37° C.; no growth at 10° and 42° C. |
| NaCl tolerance | Growth at 10% but not 13% | Growth at 10% but not 13% |
| Melanoid pigment: | | |
| Peptone-yeast extract iron agar (ISP-6) | − | − |
| Tyrosine agar (ISP-7) | − | − |
| Tryptone-yeast extract broth (ISP-1) | − | − |

The compounds of the present invention may be produced by culturing Streptomyces microorganisms in appropriate media, preferably in a liquid, submerged, agitated fermentation with a culture medium containing a suitable source of carbon and a source of nitrogen. Media which are useful include an assimilable source of carbon such as starch, sugar, molasses, glycerol, a combination of glucose plus molasses, etc.; an assimilable source of nitrogen such as protein, protein hydrolysate, pol,vpeptides, amino acids, peptone plus yeast extract or whole yeast, etc.; and other organic and inorganic ingredients which can be added to stimulate production of the dorrigocins. For example, inorganic anions and cations including potassium, magnesium, calcium, ammonium, sulfate, carbonate, phosphate and chloride may be added to the medium. Further, buffers such as calcium carbonate can be added to aid in controlling the pH of the fermentation medium. Aeration may be provided by forcing sterile air through the fermentation medium. Agitation can be provided by shaking the container or by stirring the culture, as for example with a mechanical stirrer. Fermentation is generally carded out in a temperature range of from about 20° C. to about 35° C. The pH of the fermentation is preferably maintained between 3 and 9. The compound is produced and accumulated between 3 and 14 days after inoculation of the fermentation.

Subsequent to the fermentation process, the antifungal components of the fermentation broth can be extracted by adsorption onto a polystyrene resin such as AMBERLITE XAD-2, XAD-4 or XAD-16 or Mitsubishi DIAION HP-20 resins. Partial purification of the active compounds can be achieved by sequential duration of the resin with organic solvents such as ethyl acetate, ethanol and methanol in order to selectively remove the desired organic compounds. The extracts may be flirter purified by use of various partitioning solvent systems, such as, for example, chloroform/methanol/water, hexane/ethyl acetate/methanol/water, or ethanol/ethyl acetate/water. Final purification and separation of individual components can be achieved by countercurrent chromatography in solvent systems such as, for example, ethyl acetate/ethanol/Water, chloroform/methanol/water, or chloroform/carbon tetrachloride/methanol/water.

The compounds, processes and uses of the present invention will be better understood in connection with the following examples, which are intended as an illustration of and not a limitation upon the scope of the invention. Both below and throughout the specification, it is intended that citations to the literature are expressly incorporated by reference.

EXAMPLE 1

Culture Maintenance and Fermentation of NRRL 18993

NRRL 18993 was maintained as a frozen inoculum stock by freezing a portion of the original inoculum and storing it at −70° C. The seed medium (Table 4) was used for seed growth and the fermentation medium (Table 5) was used for production of the dorrigocins.

The seed flasks were prepared by dispensing 600 mL of the seed medium (Table 4) into 2-liter Edenmeyer flasks. The flasks were stefifized for 35 minutes at 121° C., 15 psi.

Inoculum for the fermentation was prepared by inoculating 2.5 mL of the frozen inoculum into seed flasks containing 600 mL of the seed medium (Table 4). The seed flasks were incubated for 72 hours at 28° C. on a rotary shaker, operated at 225 rpm, with a stroke of 2 inches.

Thirty liters of fermentation medium (Table 5) were prepared in a 42-liter LH Fermentation stainless steel stirred fermentor and sterilized at 121° C. and 15 psi for 1 hour. Antifoam agent XFO-37 1 (Ivanhoe Chemical Co., Mundelein, Ill.) was added initially at 0.01%, then was available on demand. The fennentor was inoculated with 1500 mL of the seed flask growth. The temperature was controlled at 28° C. The agitation rate was 250 rpm and the air flow was 0.7 vol/vol/min. The head pressure was maintained at 5 psi. The fermentation was terminated at five days. The harvest volume was 27 liters.

TABLE 4

| Seed Medium (per Liter) | |
| --- | --- |
| Ingredients | Grams |
| Glucose monohydrate | 15.0 |
| Soy flour (Cargill, Inc., Minneapolis, MN) | 15.0 |
| Yeast Extract (Difco Laboratories, Detroit, MI) | 1.0 |

TABLE 4-continued

| Seed Medium (per Liter) | |
| --- | --- |
| Ingredients | Grams |
| NaCl | 1.0 |
| CaCO$_3$ | 1.0 |
| Distilled water was added to achieve a volume of 1 liter, and the pH was not adjusted. | |

TABLE 5

| NRRL 18993 Fermentation Medium | |
| --- | --- |
| Ingredients | Grams |
| Glucose monohydrate | 15.0 |
| Soybean meal (Archer Daniels Midland, Decatur, IL) | 20.0 |
| Yeast Extract (Difco Laboratories, Detroit, MI) | 5.0 |
| CaCO$_3$ | 2.0 |
| Distilled water was added to achieve a volume of 1 liter, and the pH was not adjusted. | |

EXAMPLE 2

Isolation of DordgoCins A and B

As described in EXAMPLE 1, the culture NRRL 18993 was grown in stirred culture for 5 days. To the whole broth was added 3 liters of XAD-16 resin, and the mixture was stirred for 16 hours. The resin was washed with water and the organic materials were eluted with 12 liters of methanol. This methanol eluate was concentrated to dryness and partitioned in a solvent mixture consisting of 1 liter each of chloroform, methanol and water. The upper layer from this partition was concentrated to dryness, and the residue was triturated sequentially with ethyl acetate, methanol and water. The methanol-soluble material was partitioned between hexane and methanol (0.5 liters and 0.25 liters respectively). The methanol layer from this partition was concentrated to dryness, and the residue was partitioned in a solvent mixture consisting of 0.2 liters each of hexane, ethyl acetate, methanol and water. The lower layer from this partition was concentrated to dryness, and the residue was chromatographed over a Sephadex LH-20 resin column developed with methanol. Active fractions from this column were combined and concentrated to a pale brown oil. his oil was subjected to countercurrent chromatography on an Ito multi-layered coil planet centrifuge in a solvent system of chloroform/methanol/water (1:1:1) with the lower layer stationary. Active fractions from this column were combined and concentrated to a pale yellow oil. This oil was subjected to countercurrent chromatography on an Ito multi-layered coil planet centrifuge in a solvent system of ethyl acetate/ethanol/water (3:1:2) with the lower phase stationary. Active fractions from this column were combined and concentrated to a clear oil. This oil was subjected to countercurrent chromatography on an Ito multi-layered coil planet centrifuge in a solvent system of chloroform/carbon tetrachloride/methanol/water ( 1:1:1:1) with the lower layer stationary. Active fractions from this column were combined based upon their thin layer chromatography behavior to yield pure Dorrigocins A (38 mg) and B (25 mg).

EXAMPLE 3

Alternate Isolation of Dorrigocins A and B

Upon completion of a fermentation as described in EXAMPLE 1, to the whole broth was added 3 liters of XAD-16 resin, and the mixture was stirred for 16 hours. The resin was washed with water and the organic materials were eluted with 12 L of methanol. The methanol eluate was concentrated to dryness, and the residue was triturated sequentially with 1 liter portions of ethyl acetate, methanol, and water. The methanol soluble material was partitioned in a solvent mixture consisting of hexane, ethyl acetate, methanol and water (0.2 liters of each). The lower layer from this partition was concentrated to dryness, and the residue was chromatographed over a SephadexLH-20 resin column which was developed with methanol. Active fractions from this column were combined and concentrated to a pale oil. This oil was subjected to countercurrent chromatography on an Ito multi-layered coil planet centrifuge in a solvent system of chloroform/methanol/water (1:1:1) with the lower layer stationary. Active fractions from this column were combined and concentrated to an oil. This oil was subjected to countercurrent chromatography on an Ito multi-layered coil planet centrifuge in a solvent system of ethyl acetate/ethanol/water (3:1:2) with the lower phase stationary. Active fractions from this column were combined based upon their TLC behavior to yield Dorrigocin A (8 mg) and Dorrigocin B (6 mg).

EXAMPLE 4

Physico-Chemical Characterization

The compounds of the invention were characterized using IR, UV, $^1$H and $^{13}$C NMR spectroscopy, with the following results:

Dorrigocin A (the compound of Formula Ia, above), $C_{27}H_{42}NO_8$, clear oil, $[\alpha]_D=+91°$ (c=0.13, MeOH), had an Rf of 0.71 in MeOH, an Rf of 0.34 in acetone and an Rf of 0.24 in EtOAc/MeOH (4/1), and was readily soluble in methanol and dimethylsulfoxide. An ultraviolet spectrum acquired in methanol or acidic methanol has $\lambda_{max}=204$ nm ($\epsilon=9,300$). An ultraviolet spectrum acquired in basic methanol has $\lambda_{max}=209$ nm ($\epsilon=11,000$). $^1$H and $^{13}$C NMR data are tabulated in Tables 6 and 7 below. An infrared spectrum acquired as a thin film contains bands at $v_{max}=3,446, 3,203, 3,085, 2,966, 2,930, 2,876, 1,708, 1,698, 1,657, 1,451, 1,375, 1,263, 1,197, 1,149, 1,112, 1,073, 1,048, 982, 871$ and $753$ cm$^{-1}$.

Dorrigocin B (the compound of Formula Ib, above), $C_{27}H_{42}NO_8$, a clear oil, $[\alpha]_D=+16°$ (c=0.33, MeOH), had an Rf of 0.73 in MeOH, an Rf of 0.38 in acetone and an Rf of 0.46 in EtOAc/MeOH (4:1) and was readily soluble in methanol and dimethylsulfoxide. An ultraviolet spectrum acquired in methanol or acidic methanol has $\lambda_{max}=206$ nm ($\epsilon=12,000$). An ultraviolet spectrum acquired basic methanol has; $\lambda_{max}=208$ nm (e=14,000). $^1$H and $^{13}$C NMR data are tabulated in Tables 6 and 7 below. An infrared spectrum acquired as a thin film contains bands at $v_{max}=3,452, 3,207, 3,093, 2,971, 2,930, 2,827, 1,710\ 1,700, 1,657, 1,450, 1,381, 1,262, 1,149, 1,114, 1,087, 982, 878$ and $752$ cm$^{-1}$.

TABLE 6

| $^1$H NMR Data for Dorrigocins A and B (in CD$_3$OD) | | |
|---|---|---|
| Proton on carbon # | Dorrigocins A | Dorrigocins B |
| 2 | 5.81(d, 1H, J=15.5) | 5.83(d, 1H, J=15.5) |
| 3 | 6.92(dt, 2H, J=15.5, 6.7) | 6.90(dt, 1H, J=15.5, 6.9) |
| 4 | 2.36(mult, 2H) | 2.32(mult, 2H) |
| 5 | 2.30(mult, 2H) | 2.28(mult, 2H) |
| 6 | 5.71(dt, 1H, J=15.5, 6.5) | 5.76(dt, 1H, J=15.5, 6.5) |
| 7 | 5.49(brdd, 1H, J=15.5, 8.6) | 5.23(ddt, 1H, J=15.5, 8.6, 1.2) |
| 8 | 3.54(dd, 1H, J=8.6, 4.1) | 3.49(dd, 1H, J=8.6, 2.4) |
| 9 | 3.21(dd, 1H, J=6.9, 4.1) | 3.34(dd, 1H, J=8.2, 2.4) |
| 10 | 2.71(dq, 1H, J=9.9, 6.9) | 1.74(mult, 1H) |
| 11 | 5.28(d, 1H, J=9.9) | 3.96(d, 1H, J=8.2) |
| 13 | 4.00(d, 1H, J=9.8) | 5.28(d, 1H, J=10.2) |
| 14 | 2.77(dq, 1H, J=9.8, 6.9) | 3.51(d, 1H, J=10.2) |
| 16 | 2.60(mult, 2H) | 2.49(mult, 2H) |
| 17 | 1.61(mult, 2H) | 1.57(mult, 2H) |
| 18 | 1.38(mult, 2H) | 1.35(mult, 2H) |
| 19 | 2.14(mult, 1H) | 2.10(mult, 1H) |
| 20, 25 | 2.62(mult, 1H) 2.31(mult, 1H) | 2.63(mult, 1H) 2.30(mult, 1H) |
| 22 | 0.97(d, 3H, J=6.7) | 0.91(d, 3H, J=7.0) |
| 23 | 1.62(brs, 3H) | 1.64(brs, 3H) |
| 24 | 0.82(d, 3H, J=7.2) | 1.10(d, 3H, J=6.5) |
| 8-OCH$_3$ | 3.22(s, 3H) | 3.24(S, 3H) |

TABLE 7

| $^{13}$C NMR Data for Dorrigocin A and B (in CD$_3$OD) | | |
|---|---|---|
| Carbon # | Dorrigocin A | Dorrigocin B |
| 1 | 170.5(Q) | 170.8(Q) |
| 2 | 123.6(CH) | 123.9(CH) |
| 3 | 149.5(CH) | 149.2(CH) |
| 4 | 32.7(CH$_2$) | 32.6(CH$_2$) |
| 5 | 31.9(CH$_2$) | 31.9(CH$_2$) |
| 6 | 135.1(CH) | 136.4(CH) |
| 7 | 130.2(CH) | 129.0(CH) |
| 8 | 84.4(CH) | 86.1(CH) |
| 9 | 78.9(CH) | 75.8(CH) |
| 10 | 35.8(CH) | 38.3(CH) |
| 11 | 133.5(CH) | 80.6(CH) |
| 12 | 135.8(Q) | 140.2(Q) |
| 13 | 81.8(CH) | 127.8(CH) |
| 14 | 50.1(CH) | 47.2(CH) |
| 15 | 216.5(Q) | 213.7(Q) |
| 16 | 43.6(CH$_2$) | 41.4(CH$_2$) |
| 17 | 21.1(CH$_2$) | 21.6(CH$_2$) |
| 18 | 35.2(CH$_2$) | 35.3(CH$_2$) |
| 19 | 31.5(CH) | 31.5(CH) |
| 20, 25 | 38.5(CH$_2$) | 38.6(CH$_2$) |
| 21, 26 | 175.5(Q) | 175.5(Q) |
| 22 | 16.4(CH$_3$) | 8.4(CH$_3$) |
| 23 | 10.8(CH$_3$) | 12.3(CH$_3$) |
| 24 | 14.5(CH$_3$) | 16.4(CH$_3$) |
| 8-OCH$_3$ | 56.4(CH$_3$) | 56.2(CH$_3$) |

EXAMPLE 5

In Vitro Assay of Antifungal activity

Minimal inhibitory concentrations (MICs) were determined by an agar dilution method. The test compounds were serially diluted in MeOHand 0.2 ml portions were mixed with 20 ml of molten, cooled Sabouraud dextrose agar (Difco). Yeast cell inoculum was prepared by growing cultures on Sabouraud dextrose agar for 18 hours at 32° C. and suspending the cells in phosphate buffered saline. Filamentous fungi were grown under the same conditions for 4 days to obtain spores. The inoculum level for all cultures was adjusted to $10^4$ cells using a Petroff-Hauser cell counter. The glutarimide antifungal compound cycloheximide was used as a control. Inoculated test plates were incubated at 32° C. and exaed after 20 hours. The results are shown in table 8.

TABLE 8

In vitro Antifungal Activity of Dorrigocins A & B MIC Values (μg/ml)

| Microorganism | Dorrigocin A | Dorrigocin B | Cyclo-heximide |
|---|---|---|---|
| *Candids albicans* ATCC 10231 | >100 | >100 | >100 |
| *Candids albicans* 579A | >100 | >100 | >100 |
| *Candids albicans* ATCC 38247 | >100 | >100 | >100 |
| *Candids tropicalis* NRRL-Y-112 | >100 | >100 | 0.4 |
| *Torulopsis glabrata* ATCC 15545 | >100 | >100 | 0.4 |
| *Saccharomyces cereviseae* GS1-36 | >100 | >100 | <0.05 |
| *Aspergillus niger* ATCC 16404 | 25 | 12.5 | 1.6 |
| *A. fianigatus* ATCC 26430 | 25 | 12.5 | 1.6 |
| *A. flavus* NRRL 6541 | >100 | 100 | 50 |
| *A. parasiticus* NRRL 13539 | >100 | 100 | 25 |
| *Fusarium moniliforme* AARC 0397 | 100 | 50 | 0.8 |
| *F. solani* AARC 0353 | 25 | 25 | 0.8 |

EXAMPLE 6

In Vitro Assay Of Antitumor Activity

The antitumor activity of Dorrigocins A and B was demonstrated using K-ras-transformed NIH/3T3 mouse fibroblasts. Transformed cells are typically rounded when the mutant ras gene is expressed. Nomml cells, on the other hand, are flat and adhere to the bottom of a tissue culture plate. The compounds of the present invention were shown to cause reversion of transformed, tumor-type cells to cells having normal morphology in assays carried out as follows:

Normal and transformed NIH/3T3 cells were cultured in Dulbecco's modified Eagle medium containing 10% fetal bovhe serum, and gentamicin 50 μg/ml at 37° C. in 5% $CO_2$. Ras transformants also contained 500 μM G418. To test the effect of Dorrigocins, $2\times10^4$ cells were added to 24 well microtiter plates and incubated for 24 hours at 37° C. when the cells had uniformly adhered to the microtiter tray, various concentrations of Dorrigocin A and B dissolved in DMSO, were added and the plates incubated at 37° C. for an additional 48 hours. Cellular morphology was examined microscopically and the average number of transformed foci per field was determined by counting at least 6 separate fields. These foci represent transformed cells that were unaffected by the addition of compound.

The average number of transformed foci per field under 50x magnification is shown in Table 9. Control experiments with DMSO showed no reduction in the number of transformed foci over time. The addition of Dordgocin A and B caused transformed cells to revert to a morphology resembling that of normal cells. This effect was dose-dependent, i.e., was dependent on the amount of compound present. Dorrigocin A was more effective than Dorrigocin B in causing morphology reversion and the reduction in the number of foci.

TABLE 9

Effect of Dorrigocins A and B on the Number of Foci Produced by K-ras-Transformed NIH/3T3 Mouse Fibroblasts

| Cell Line | Compound dose (μg/ml) | Transformed foci percentage |
|---|---|---|
| NIH/3T3 | none | 0 |
| NIH/3T3 K-ras | none | 100 |
| NIH/3T3 K-ras | Dorrigocin A | |
| | 10 | 22 |
| | 0.4 | 26 |
| | 0.08 | 76 |
| | Dorrigocin B | |
| | 10 | 72 |
| | 0.4 | 96 |

While not wishing to be limited by theory, it is believed that the morphology reversion described above results from improper post-translational modification of the oncogenic ras protein, thus resulting in its likely accumulation in the cytoplasm where it would be unable to cause cell u:ansformation. Consequently, it is expected that the compounds of the present invention would be capable of slowing tumor growth and inhibiting metastasis in cancers caused by mutations in the ras gene.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art, and may be made without departing from the spirit and scope thereof.

What is claimed is:

1. A compound having the formula

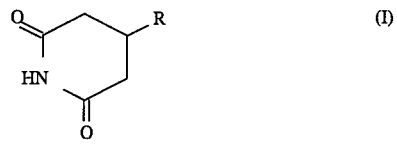

or a pharmaceutically acceptable salt, ester, amide or prodrug thereof, wherein R is selected from the group consisting of

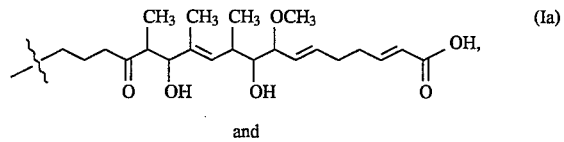

and

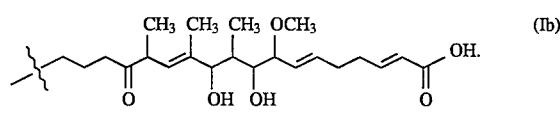

2. A compound according to claim 1 herein R is

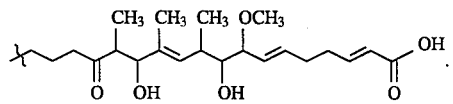

3. A compound according to claim 1 wherein R is

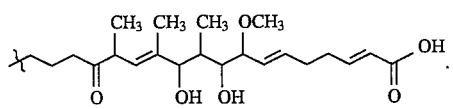

4. A pharmaceutical composition comprising a compound according to claim 1 in combination with a pharmaceutically acceptable carrier.

5. A method of treating fungal infections in a patient in need of such treatment, comprising administering to the patient a therapeutically effective amount of a compound according to claim 1.

* * * * *

UNITED STATES PATENT AND TRADEMARK OFFICE
CERTIFICATE OF CORRECTION

PATENT NO.  : 5,484,799
DATED       : January 16, 1996
INVENTOR(S) : J. E. Hochlowski, M. Jackson, S. K. Kadam,
              J. P. Karwowski, J. B. McAlpine It is certified that error appears in the above-indentified patent and that said Letters Patent is hereby corrected as shown below:

Column 2, line 9, delete "desked" and insert --desired--.

Column 16, line 60, delete "herein" and insert --wherein--.

Signed and Sealed this

First Day of October, 1996

Attest:

BRUCE LEHMAN

*Attesting Officer*    Commissioner of Patents and Trademarks